United States Patent [19]
Lok et al.

[11] Patent Number: 5,576,432
[45] Date of Patent: Nov. 19, 1996

[54] PROCESS FOR THE MANUFACTURE OF DIHYDROPYRIMIDINES

[75] Inventors: Roger Lok; Antony J. Williams, both of Rochester, N.Y.

[73] Assignee: Eastman Kodak Company, Rochester, N.Y.

[21] Appl. No.: 363,148

[22] Filed: Dec. 23, 1994

[51] Int. Cl.$^6$ .................... C07D 498/04; C07D 513/04; C07D 517/04

[52] U.S. Cl. .................... 544/250; 544/252; 544/254; 544/255; 544/256; 544/282; 544/356; 546/159; 546/180; 548/121; 548/152; 548/161; 548/190; 548/217; 548/221; 548/222; 548/233; 548/235; 548/307.4; 548/483; 564/383; 564/509

[58] Field of Search .................... 544/250, 252, 544/254, 255, 256, 282

[56] References Cited

U.S. PATENT DOCUMENTS

| | | | |
|---|---|---|---|
| 3,893,962 | 7/1975 | Munshi et al. | 96/66.3 |
| 4,451,557 | 5/1984 | Lok et al. | 430/505 |
| 4,471,117 | 9/1984 | Sipido | 544/250 |
| 5,192,654 | 3/1993 | Hioki et al. | 430/576 |

FOREIGN PATENT DOCUMENTS

0465728A1  1/1992  European Pat. Off. .

OTHER PUBLICATIONS

Engel et al, *Chemical Abstracts*, vol. 108, No. 56121.
Lutz, *Chemical Reviews*, vol. 84 pp. 205–247 (1984).
Richardson *Fused Pyrimidines as Potential Antimicrobic Agents* Journal of Medicinal Chemistry, vol. 15, Dec. 1972, pp. 1203–1206.
Alaimo *The Synthesis of Some 4H–Pyrimido[2,1–b]benzothiazol–4–ones* J. Heterocyclic Chemistry, vol. 10, Oct. 1973, pp. 769–772.
Wade, *Reaction of 2–Aminobenzazoles with Dimethyl 2–Aminofumarate. Synthesis and Nuclear Magnetic Resonance Spectroscopy of 4–Oxopyrimido[2,1–b]benzazoles*, J. Org. Chem., vol. 44, No. 11, 1979 pp. 1811–1816.
*Helvetica Chimica Acta.*, vol. 56, No. 8, 1973, pp. 2981–3004, Koch–Pomeranz et al.
*A Convenient Synthesis of 3–Methylthiazolo [3,2–1]benzimidazoles, 3–Benzylthiazolo[3,2–a]benzimidazoles, and 4–Phenylthiazeno[3,2–a}benzimidazoles*, Synthesis, Mar. 1976, p. 189, Balasubramanian et al.

Primary Examiner—Emily Bernhardt
Attorney, Agent, or Firm—Sarah Meeks Roberts

[57] ABSTRACT

A process of preparing a dihydropyrimidine compound of the structure (I):

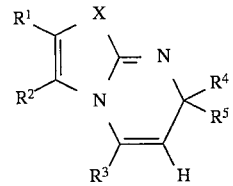

wherein $R^1$ and $R^2$ are bonded together to form an aromatic or heterocyclic ring, which may be substituted or unsubstituted, or are individually selected from the group consisting of hydrogen, or a substituted or unsubstituted aliphatic, carbocyclic, or heterocyclic group;

$R^3$, $R^4$ and $R^5$ are individually selected from the group consisting of hydrogen or a substituted or unsubstituted aliphatic, carbocyclic or heterocyclic group; and X represents the atoms necessary to form a 5 or 6 membered heterocyclic ring, and is selected from the group consisting of oxygen, sulfur, selenium,

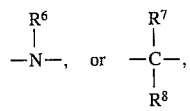

wherein $R^6$, $R^7$, and $R^8$ are individually selected from the group consisting of a substituted or unsubstituted aliphatic, carbocyclic or heterocyclic group; comprising combining a compound (A) of the structure:

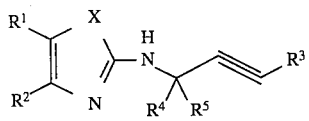

wherein X, $R^1$, $R^2$, $R^3$, $R^4$, $R^5$, $R^6$, $R^7$, and $R^8$ are as previously defined, with a catalytic amount of a Group 11 or 12 metal cation catalyst at a temperature of less than about 50° C. and in the presence of an organic solvent, to form compound (I).

12 Claims, No Drawings

PROCESS FOR THE MANUFACTURE OF DIHYDROPYRIMIDINES

FIELD OF THE INVENTION

This invention relates to processes for preparing certain dihydropyrimidine compounds. Such compounds are capable of being utilized in photographic materials to obtain advantageous photographic effects.

BACKGROUND OF THE INVENTION

Photographic emulsions consist of microcrystals of silver halide which are sensitive to light. After exposure to light, the emulsions are developed to form either a black and white or dye image, the density of which is generally dependent upon the amount of light that has exposed the microcrystals, and the inherent sensitivity of such crystals.

In an effort to improve the performance of photographic emulsions, the photographic industry has attempted to improve emulsion sensitivity. Much of its effort has focused on the treatment of photographic emulsion microcrystals with certain chemicals to enhance their sensitivity. Additional effort has been directed to modification of the morphology and/or composition of the microcrystals to make them more responsive to light, or more susceptible to development.

Dihydroheteroaromatic compounds have been reported as useful in the preparation of photographic emulsions. For example, in U.S. Pat. No. 5,192,654, dihydropyridines are utilized to ameliorate the effect of desensitization from certain spectral sensitizing dyes. In U.S. Pat. No. 3,893,862, 1,4 and 1,2-dihydropyridines are found to be useful as latent image amplifiers.

Through extensive research, the present inventors have found that additional types of dihydroheteroaromatic compounds may be incorporated into photographic emulsions to effectuate a desired photographic response. It has been found that certain dihydropyrimidines provide the photographic industry the opportunity to obtain improved sensitivity in photographic emulsions. With this discovery, there is the need to find a practical and effective way to manufacture such compounds.

The synthesis and stability of dihydropyrimidines have been extensively explored. Many of the known processes for synthesis involve the formation of a pyrimidine ring via the condensation of an acyclic carbonyl compound with a nitrogen containing compound. Typically, reactions of this sort involve high temperatures or strongly alkali conditions.

Other methods of forming dihydropyrimidines involve reduction of aromatic pyrimidines with complex metal hydrides or organometallic reagents that are costly for manufacturing. Other methods call for the addition of ammonia at −45° C., a condition that is difficult and expensive to maintain during manufacturing. Still others require reactants that are not readily available or, because of the general lack of stability of dihydropyrimidines, involve processes that provide unacceptable yields.

Fused tricyclic pyrimidines have been reported by Richardson, "Fused Pyrimidines as Potential Antimicrobic Agents" Journal Of Medicinal Chemistry, Vol. 15, December 1972, pp. 1203–1206; Alaimo "The Synthesis of Some 4H-Pyrimido[2,1-b]benzothiazol-4-ones" J. Heterocyclic Chemistry, Vol. 10, October 1973, pp. 769–772; and Wade, "Reaction of 2-Aminobenzoles with Dimethyl 2-Aminofumarate. Synthesis and Nuclear Magnetic Resonance Spectroscopy of 4-Oxopyrimido[2,1-b]benzazoles", J. Org. Chem., Vol. 44, No. 11, 1979 pp. 1811–1816, as well as in other chemical literature. Most of the syntheses disclosed involve the thermal condensation of 2-amino heteroazoles with unsaturated carbonyl compounds.

In U.S. Pat. No. 4,471,117, 3,4-dihydro-2H-pyrimido[2,1-b]benzothiazoles useful as antidepressants and anti-Parkinson's agents are disclosed. The compounds are prepared by known cyclization procedures involving heating of appropriately substituted alcohols or their halogenated analogs. In EP 0 465 728, mercapto substituted pyrimidines are disclosed as useful in the stabilization of silver halide emulsions comprising tabular grains. Such compounds are prepared by known methods.

It is known that certain alkynylamines can undergo a thermal Claisen rearrangement reaction to yield a mixture of tetrahydrobenzoquinolines and benzoquinolines. However, like many of the methods of forming dihydropyrimidines, such methods often require high temperatures, typically in the order of 100° C. or more, or acidic or basic conditions in order for the reactions to occur. It is also known from Koch-Pomeranz "The Arrangement of Propargyl Phenyl Ethers Catalyzed by Silver Ions" Helvetica Chimica Acta., Vol. 56, No. 8, 1973, pp. 2981–3004 that propargyl phenyl ethers catalyzed by silver ions can undergo rearrangement reaction in benzene or chloroform to form the corresponding cyclic structure. Again, such reactions are typically carried out under conditions of high temperature. When carried out at lower temperatures, the product yield is severely curtailed. Additional metal catalyzed cyclization reactions involving alkynyl groups are disclosed by Balasubramanian and Nagarajan, "A Convenient Synthesis of 3-Methylthiazolo [3,2-1]benzimidazoles, 3-Benzylthiazolo[3,2-a]benzimidazoles, and 4-Phenylthiazeno[3,2-a}benzimidazoles", Synthesis, March 1976, pp. 189.

Despite the relative comprehensiveness of the art surrounding the synthesis of dihydropyrimidines, there has yet to be provided a satisfactory synthesis that can be used for the large scale production necessary in the photographic industry. Further, there has yet to be provided a synthesis that can be practiced at low temperature, with non-toxic solvents, and with few reactants.

SUMMARY OF THE INVENTION

Accordingly, it is an object of the present invention to provide a process by which dihydropyrimidines can be synthesized.

Further, it is an object of the present invention to provide such a method wherein it can be performed economically, at low temperature, in the presence of non-toxic solvents, and with few reactants.

These and other objects of the invention are achieved by a process of preparing a dihydropyrimidine compound of the structure (I):

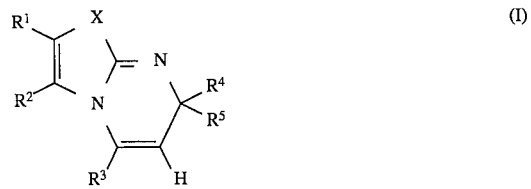

wherein $R^1$ and $R^2$ are bonded together to form an aromatic or heterocyclic ring, which may be substituted or unsubstituted, or are individually selected from the group consisting of hydrogen, or a substituted or unsubstituted aliphatic, carbocyclic, or heterocyclic group;

$R^3$, $R^4$ and $R^5$ are individually selected from the group consisting of hydrogen or a substituted or unsubstituted aliphatic, carbocyclic or heterocyclic group; and X represents the atoms necessary to form a 5 or 6 membered heterocyclic ring, and is selected from the group consisting of oxygen, sulfur, selenium,

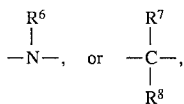

wherein $R^6$, $R^7$, and $R^8$ are individually selected from the group consisting of a substituted or unsubstituted aliphatic, carbocyclic or heterocyclic group;

comprising combining a compound (A) of the structure:

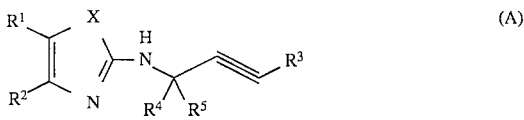

wherein X, $R^1$, $R^2$, $R^3$, $R^4$, $R^5$, $R^6$, $R^7$, and $R^8$ are as previously defined, with a catalytic amount of a Group 11 or 12 metal cation catalyst, at a temperature of less than about 50° C. and in the presence of an organic solvent, to form compound (I).

DETAILED DESCRIPTION OF THE INVENTION

In the general embodiment of the invention, a dihydropyrimidine compound is formed by the cyclization of a heterocyclic alkynylamine, compound (A), in the presence of an organic solvent and a metal ion catalyst. Specifically, the dihydropyrimidine compound is a 1,4-dihydropyrimidine fused to a heterocycle containing at least one nitrogen atom which, together with the second nitrogen atom of the pyrimidine ring, forms a N—C=N moiety. A 1,4-dihydropyrimidine is meant to describe the positions of saturation such that they are in the 1 and 4 positions of the pyrimidine ring. These positions are illustrated in formula (II)

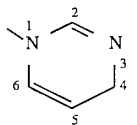

wherein positions 1 and 2 signify the positions of attachment to the fused heterocyclic ring.

The dihydropyrimidine compound synthesized by practice of the invention has the structure(I):

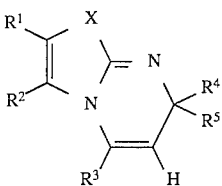

wherein $R^1$ and $R^2$ represent the atoms which, when bonded together, form an aromatic or heterocyclic ring, which may be substituted or unsubstituted, or are individually selected from the group consisting of hydrogen, or a substituted or unsubstituted aliphatic, carbocyclic, or heterocyclic group;

$R^3$, $R^4$ and $R^5$ are individually selected from the group consisting of hydrogen or a substituted or unsubstituted aliphatic, carbocyclic or heterocyclic group; and X represents one or two atoms necessary to form a 5 or 6 membered heterocyclic ring, each atom being selected from the group consisting of oxygen, sulfur, selenium,

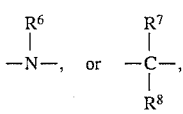

wherein $R^6$, $R^7$, and $R^8$ are individually selected from the group consisting of a substituted or unsubstituted aliphatic, carbocyclic or heterocyclic group. Aliphatic, carbocyclic, and heterocyclic groups are defined in accordance with the definitions set forth in Grant and Hackh's *Chemical Dictionary*, fifth ed., McGraw-Hill 1987, and are in accordance with general rules of chemical nomenclature.

Exemplary aliphatic groups include alkyl, alkene, and alkyne groups, specifically methyl, ethyl, propyl, butyl, pentyl, hexyl, octyl, nonyl, decyl, dodecyl, hexadecyl, octadecyl, isopropyl, t-butyl, butenyl, pentenyl, hexenyl, octenyl, dodecenyl, propynyl, butynyl, pentynyl, hexynyl, and octynyl.

Exemplary carbocyclic groups (which include aryl groups) are phenyl, tolyl, naphthyl, cyclohexyl, cyclopentyl, cyclohexenyl, cycloheptatrienyl, cyclooctatrienyl, cyclononatrienyl, cyclopentenyl, anilinyl, and anisidinyl.

Exemplary heterocyclic groups (which include heteroaryl groups) are pyrrolyl, furanyl, tetrahydrofuranyl, pyridinyl, picolinyl, piperidinyl, morpholinyl, thiadiazolyl, thiatriazolyl, benzothiazolyl, benzoxazolyl, benzimidizolyl, benzoselenozolyl, benzotriazolyl, indazolyl, quinolinyl, quinaldinyl, pyrrolidinyl, thiophenyl, oxazolyl, thiazolyl, imidazolyl, selenazolyl, tellurazolyl, triazolyl, tetrazolyl, and oxadiazolyl.

Groups suitable for substitution on each R include alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen groups, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups.

It is preferred that in the practice of the present invention $R^1$ and $R^2$ are bonded together to form a substituted or unsubstituted aromatic ring having 5 to 7 carbon atoms, or are individually selected from the group consisting of hydrogen or an alkyl having 1 to 5 carbon atoms. Also preferred is where any or all of $R^3$, $R^4$ and $R^5$ are selected from the group consisting of hydrogen, an unsubstituted alkyl, preferably having 12 or fewer carbon atoms, or an unsubstituted aryl group, preferably phenyl.

$R^6$, $R^7$ and $R^8$ are preferably individually selected from the group consisting of hydrogen or an alkyl group having 1 to 5 carbon atoms; and it is preferred that X be selected from the group consisting of oxygen, sulfur or selenium.

Examples of dihydropyrimidine compounds synthesized by practice of the invention are:

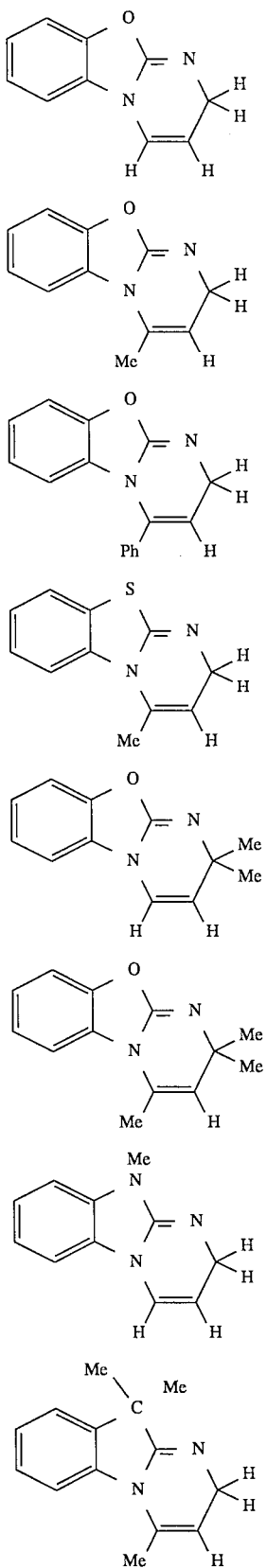

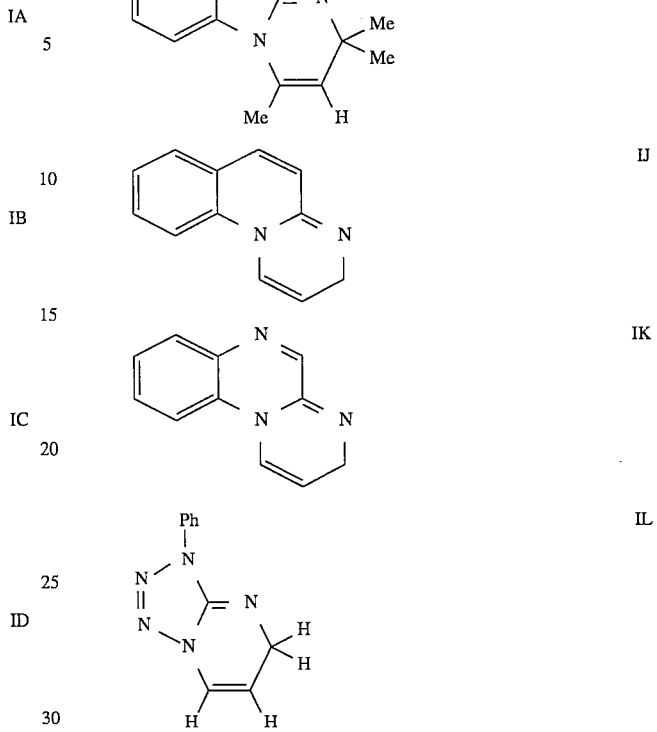

The method of synthesis of the dihydropyrimidines involves the treatment of a heterocyclic alkynylamine as represented by compound (A) with a catalytic amount of a Group 11 or 12 metal cation catalyst in an organic solvent, wherein compound (A) has the structure:

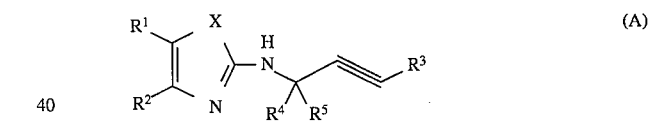

wherein X, $R^1$, $R^2$, $R^3$, $R^4$, $R^5$, $R^6$, $R^7$, and $R^8$ are as previously defined with respect to the dihydropyrimidine compound.

In a preferred embodiment, compound (A) has the structure:

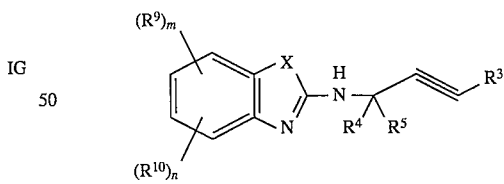

wherein
$R^9$ and $R^{10}$ individually represent a substituted or unsubstituted alkyl group;
X, $R^3$, $R^4$, and $R^5$ are as defined as above with respect to the dihydropyrimidine; and
n and m are individually 0 or 1.

In this embodiment, it is preferred that $R^3$ be selected from the group consisting of hydrogen, an unsubstituted alkyl, preferably having 12 or fewer carbon atoms, or an unsubstituted aryl group, preferably phenyl; and $R^4$ and $R^5$ are individually selected from the group consisting of hydrogen or a substituted or unsubstituted alkyl or aryl group, preferably an unsubstituted alkyl having 12 or fewer carbon atoms or phenyl. Also, $R^6$, $R^7$, and $R^8$ are preferably individually selected from the group consisting of hydrogen or an alkyl group having 1 to 5 carbon atoms, and X is selected from the group consisting of oxygen, sulfur or selenium.

Specific exemplary compounds (A) are illustrated below:

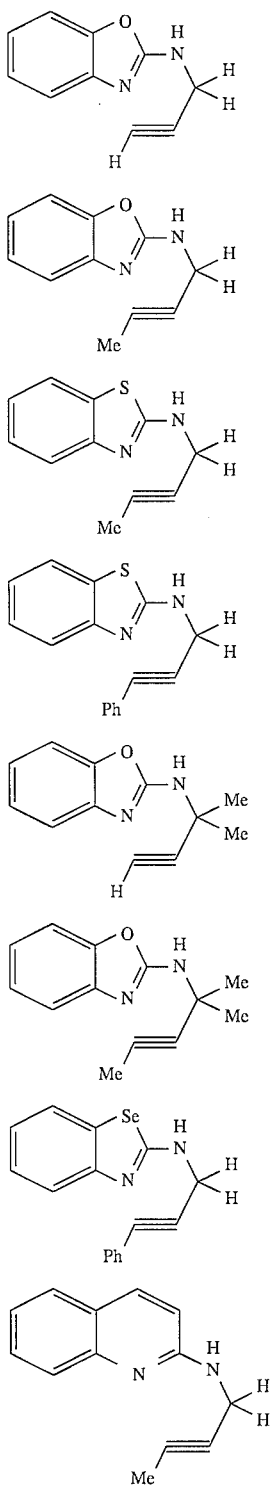

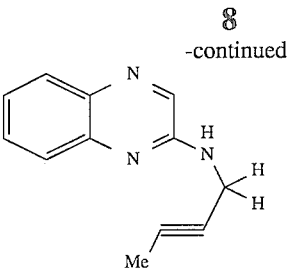

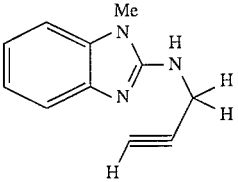

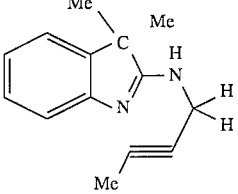

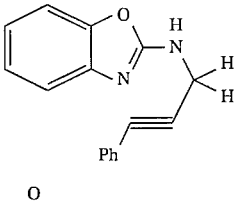

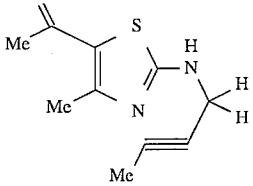

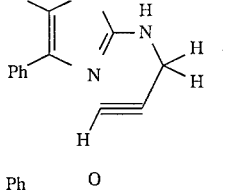

These compounds may be prepared by condensation of simple alkynylamines or their ammonium salts with a heterocycle as represented by formula III below:

wherein X, $R^1$ and $R^2$ are as described above with respect to the dihydropyrimidine compound and L is an appropriate leaving group capable of being displaced reaction by the alkynylamine or its ammonium salt. L can include any of the halogens such as Cl or Br, a thioalkyl group such as methylmercapto or ethylmercapto, and an alkyl or an aryl sulfonato group such as methylsulfonato or p-toluenesulfonato group. Preferably, the leaving group is a chloro group or a methylmercapto group. Compounds of formula (III) are commercially available or they can be prepared following procedures from standard organic textbooks or journals. A common synthetic procedure would be the conversion of the hydroxy analog of formula (III) (L=OH) using phosphoryl chloride (POCl$_3$).

Specific examples of compounds of formula (III) are:

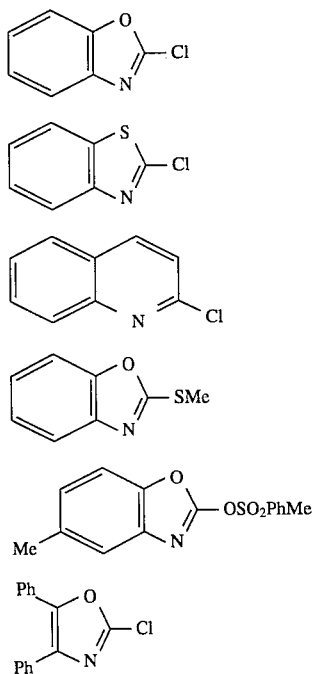

The alkynylamines utilized in the synthesis of compound (A) are primary amines containing an alkynyl group beta to the nitrogen atom as represented in formula (IV):

wherein $R^3$, $R^4$ and $R^5$ are as described previously with respect to the dihydropyrimidine compound. The ammonium salts of the above alkynylamines are also suitable for practice of the invention. The alkynylamines and their ammonium salts are available commercially or they may be prepared following known procedures in the chemical art. One method that is particularly useful is the conversion of an alkynyl halide to the alkynylamine via the Gabriel amine synthesis.

Examples of alkynylamines are illustrated as follows:

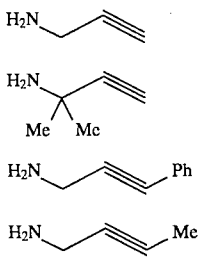

The process of the invention utilizes a metal cation as a catalyst in the production of the dihydropyrimidine compound of structure(I) from Compound (A). The metal cation enables the synthesis to be practiced quickly, in the absence of high temperature, and with little or no other reactants. Specifically, the invention may be practiced at less than about 50° C., more preferably between about 10° and about 25° C., and optimally between 12° and 20° C. By practice of the invention at low temperatures, the inventors have found a way to isolate the product and prevent its further reaction with the catalyst thus forming a photographically inactive species. Further, practice of the invention at lower temperatures allows for the production of only the 6-membered dihydropyrimidine ring as opposed to mixtures of 6 and 5-membered rings which are so prevalent in most cyclization reactions involving acetylenic heterocycles. The production of such mixtures is particularly avoided when quantities of compound A2 are catalyzed to form their corresponding dihydropyrimidine product. By practice of the invention, production of mixtures of reactants and products is also substantially avoided as the reaction proceeds rapidly to completion in the absence of any equilibrium between reactants and products. For instance, the half-life times of cyclization of A2 is on the order of fifteen minutes, and that of A5 is only three minutes, as monitored by proton nuclear magnetic resonance spectroscopy.

The catalyst involved in the present invention can be any metal cation applied to the process in the form of a cationic salt. Preferably, these include transition metal cations selected from Groups 11 and 12 of the periodic table, defined in accordance with the American Chemical Society and published in the Chemical and *Engineering News,* Feb. 4, 1985, p. 26. As such, the catalysts include cations of silver, mercury, copper, gold, and zinc. It is more preferred that the catalysts be selected from Group 11 of the periodic table, and even more preferred that they be selected from either silver or gold cations.

In the practice of the invention, the synthesis occurs in the presence of a catalytic amount of the catalyst. By catalytic amount, it is meant the amount of the catalyst necessary for the cyclization reaction to occur. This amount may vary depending on the metal cation and the solubility of the metallic salt in organic solvent. The term catalytic is taken to mean that the metal cation is not consumed in the reaction, and that in the absence of the catalyst, the cyclization reaction would proceed at a very slow rate if at all. Typically, a 1:1 equivalent of the catalyst to the heterocyclic alkynylamine is employed. However, a higher or lower ratio of catalyst to the heterocyclic alkynylamine may also be used.

The anion associated with the metal cation catalyst is generally irrelevant to the practice of the invention. However, it generally must be associated with the catalyst via a sufficiently weak bond so that it may be easily displaced in an organic solvent, thus providing the metal ion catalyst the opportunity to interact with Compound (A). Examples of suitable anions are tetrafluoroborate, hexafluorophosphate, acetate, perchlorate, trifluoroactate, and nitrate, the most preferred being tetrafluoroborate.

Specific examples of catalysts and their accompanying anions include

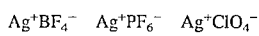
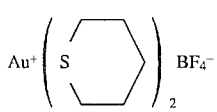
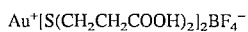
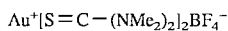
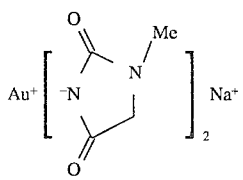
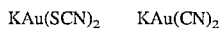
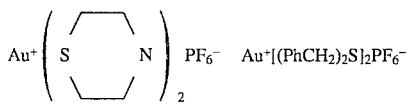
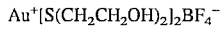
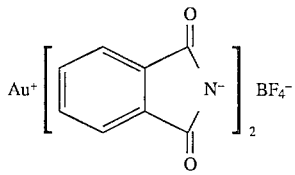

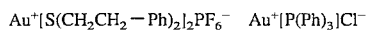

The organic solvent utilized in the invention may be any of the common organic solvents such as amides, sulfoxides, nitriles, and alcohols. Examples of suitable organic solvents include dimethyl formamide, N-methyl-2-pyrrolidone, dimethyl sulfoxide, acetonitrile, and ethyl alcohol. Among these solvents, the most preferred are acetonitrile and other polar aprotic solvents.

As described, conditions during the synthesis are generally maintained at room temperature with no heating required or other harsh conditions necessary. Thus, practice of the invention preferably occurs in an environment of neutral pH. Isolation of the resulting dihydropyrimidine is also very simple as it requires no more than the addition of the halogen salts of alkali metals (e.g., NaCl, NaBr, KI) to the solution comprising the dihydropyrimidine and catalyst and filtration. Purification may be performed by conventional recrystallization, chromatography, or sublimation. Sublimation is particularly preferred for obtaining the purest form of the dihydropyrimidine at the highest yield.

A complete representative synthesis of a dihidropyrimidine compound is shown by the following schematic, where $R^1$, $R^2$, $R^3$, $R^4$, $R^5$, X and L are as described previously, and Y is a halogen.

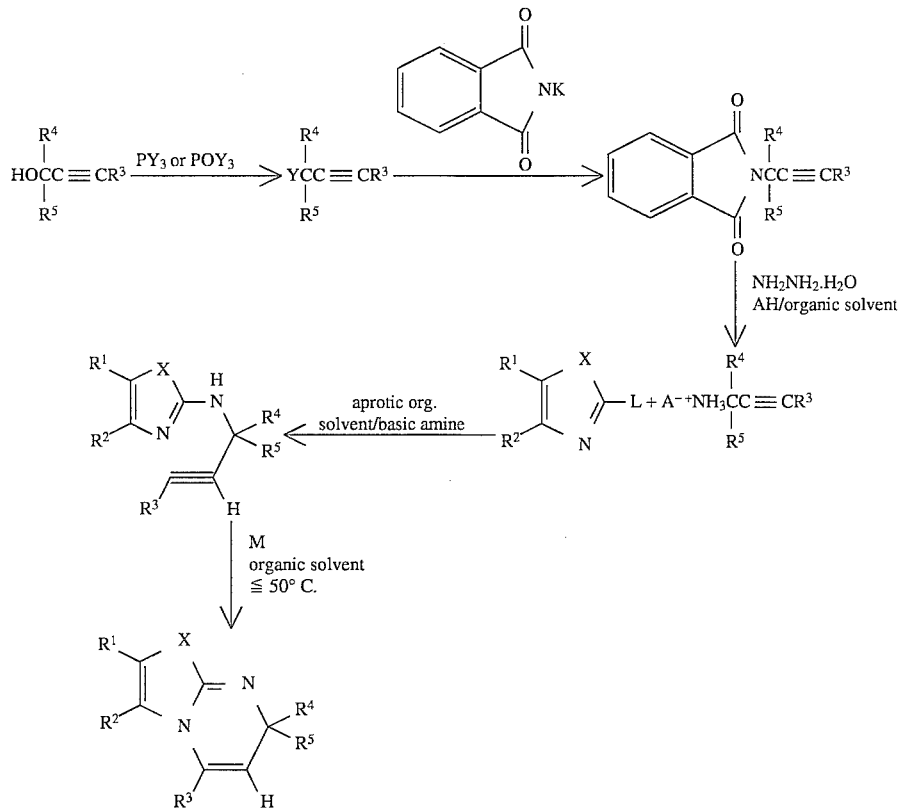

wherein A represents an organic acid anion and M represents a metal cation catalyst.

A preferred synthesis for the preparation of compound IB from readily available reactants is illustrated below

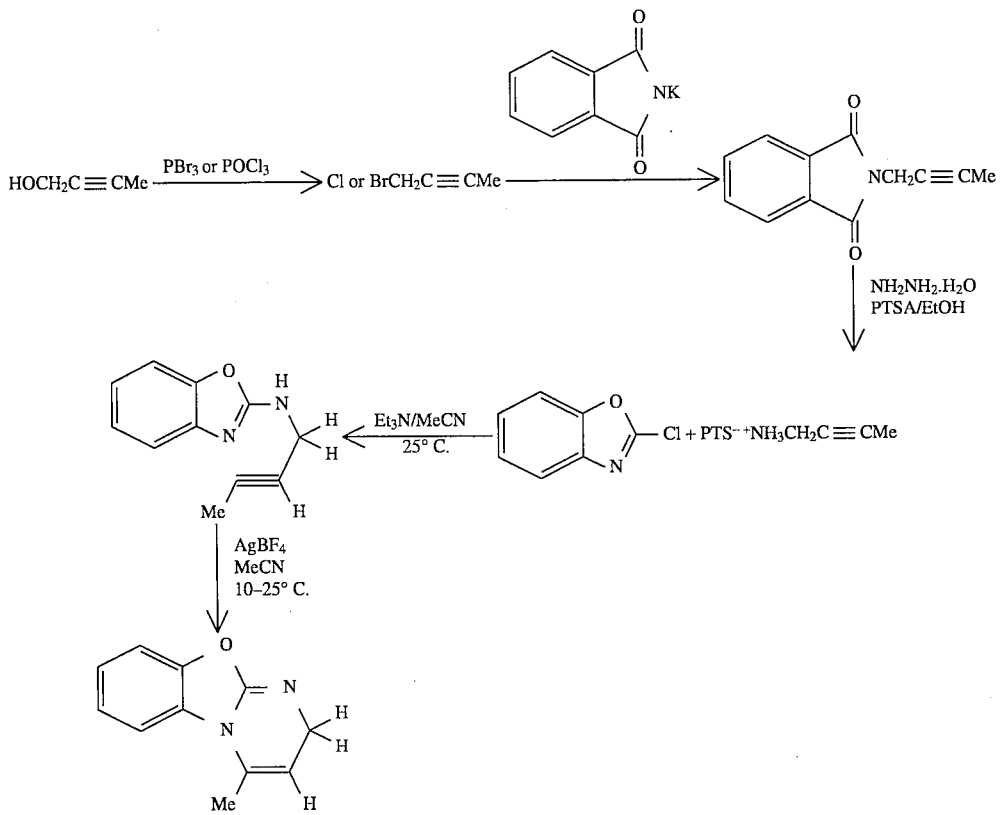

wherein PTSA represents p-toluene sulfonic acid, and PTS represents p-toluene sulfonate.

The invention may be better understood by reference to the following synthetic examples.

EXAMPLE 1

Preparation of compound (IA). A mixture of 2-propargy-laminobenzoxazole (A1, 5.16 g, 0.03 mol) and silver tetrafluoroborate (4 g, 0.02 mol) was stirred in 150 ml of dry acetonitrile at room temperature ($\cong$23° C.) overnight under nitrogen. The mixture was protected from light by an aluminum foil wrapped around the reaction flask. After 16 hrs, sodium iodide (4 g, 0.027 mol) was added to the mixture which was stirred for another 15 minutes and then filtered. The filtrate was concentrated under vacuum leaving behind a dull yellow solid. This material was triturated with methylene chloride several times each time followed by filtration. The filtrates were combined and concentrated under vacuum. A brownish yellow solid weighing 4.1 g was obtained. This solid was sublimed at 100°–125° C. under 0.07 mm Hg of pressure. The sublimate weighed 2.9 g for compound (IA). Further purification was done by slurrying the solid with a small amount of cold-dry ether. Thin layer chromatography (methylene chloride:acetonitrile 5:1, silica gel) of the solid showed a one spot homogeneous chromatogram. Elemental analysis for compound (IA) is as follows: (calculated for $C_{10}H_8N_2O$) C, 69.76; H, 4.68; N, 16.27; (found) C, 69.56; H, 4.89; N, 16.17. NMR data for (IA) is (CD$_3$CN): 6.8–7.2 (m, 4H, ArH), 6.65 (2t, $J_{AB}$=8 Hz, $J_{AX}$=2 Hz, 1H, N—CH=C), 4.95 (2t, $J_{AB}$=8 Hz, $J_{BX}$=3.5 Hz, 1H, NC=CH—), 4.35 (2d, $J_{AX}$=2 Hz, $J_{BX}$=3.5 Hz, 2H, N—CH$_2$—C) . Carbon-13 spectrum taken in deuterated chloroform shows peaks at 144.3, 109.6, 123.4, 120.8, 105.7, 129.6 (benzene ring carbons), 121.7 (—NCH=C), 104.5 (C=CH—CH$_2$), 46.7 (C=CCH$_2$), 153, (—NC=N—). Mass spectrometry data show a peak at the mass unit of 172 (molecular weight of (IA)).

EXAMPLE 2

Preparation of compound (IB). A similar procedure as for compound (IA) was used except that the reaction mixture of A2 and silver tetrafluoroborate was stirred for seven days at room temperature. The sublimed material (125°–130 ° C. under 0.07 mm Hg of pressure) showed a homogeneous one spot chromatogram (methylene chloride: acetonitrile 5:1, silica gel) and had the correct NMR spectrum: (CD$_3$CN) 7–7.3 (m, 4H, ArH), 4.76 ( 3 q, $J_{AX}$=1.6 Hz, $J_{AM}$=$J_{AM'}$=3.2 Hz, 1H, NC=CH—), 4.33 (2q, $J_{MX}$=$J_{M'X}$=1.6 Hz, $J_{AM}$=$J_{AM'}$=3.2 Hz, 2H, N—CH$_2$—C), 2.26 (3d, $J_{AX}$=$J_{MX}$=$J_{M'X}$=1.6 Hz, 3H, N—CCH$_3$=C). Compound IB weighed 2.5 g.

EXAMPLE 3

A number of different species of compound (A) were prepared and compared to analgous compounds not having acetylenic bonds (e.g. heterocylic propylamines and allylamines). The compounds were studied by proton NMR spectroscopy for their ability to form cyclized products in the presence of deuterated acetonitrile and silver tetrafluoroborate. Data in Table I show that all of the reactants utilized in the invention underwent cyclization reactions under ambient temperatures (20°–25° C.) to form dihydropyrimidines while neither the propylamine nor the allylamine benzoxazoles underwent any reaction.

TABLE I

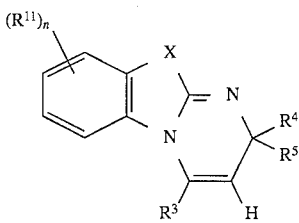

| Sample | C/I | X | $R_5$ | $R_4$ | Cyclization |
|---|---|---|---|---|---|
| 1 | C | O | H | $CH_2CH_2CH_3$ | No |
| 2 | C | O | H | $CH_2CH=CH_2$ | No |
| 3 | I | O | H | $CH_2C\equiv CH$ | Yes |
| 4 | I | O | H | $CH_2C\equiv CMe$ | Yes |
| 5 | I | O | H | $CH_2C\equiv CPh$ | Yes |
| 6 | I | O | H | $C(Me)_2C\equiv CH$ | Yes |
| 7 | I | O | Me | $CH_2C\equiv CH$ | Yes |
| 8 | I | O | CN | $CH_2C\equiv CH$ | Yes |
| 9 | I | O | Me | $CH_2C\equiv CMe$ | Yes |
| 10 | I | O | CN | $CH_2C\equiv CMe$ | Yes |
| 11 | I | S | H | $CH_2C\equiv CH$ | Yes |
| 12 | I | S | H | $CH_2C\equiv CMe$ | Yes |

C = Comparison
I = Invention

EXAMPLE 4

Various compounds (A) were treated with different metal cations and their reactions monitored by proton NMR spectroscopy as in Example 3. Data in Table II indicate that only the metal cations of the present invention serve to catalyze formation of the desired product. Further, it is demonstrated in Table II that when heat is applied to the catalyzed reaction, the desired product cannot be isolated and obtained.

TABLE II

| $R_5$ | Catalyst | Product |
|---|---|---|
| IIIA | none (comparison) | None |
| IIIA | LiCl (comparison) | None |
| IIIA | $FeCl_3$ (comparison) | None |
| IIIA | $MnCl_2$ (comparison) | None |
| IIIA | $AgBF_4$ (invention) | Yes |
| IIIA | Au(I) (invention)# | Yes |
| IIIB | Au(I) (invention)# | Yes |
| IIIA | $AgBF_4$ (comparison)* | None |

*Heat applied (60° C.)
Aurous bis(pentamethylenesulfide) tetrafluoroborate

The invention has been described in detail with particular reference to preferred embodiment, but it will be understood that variations and modifications can be effected within the spirit and scope of the invention.

What is claimed is:

1. A process of preparing a dihydropyrimidine compound of the following structure (I):

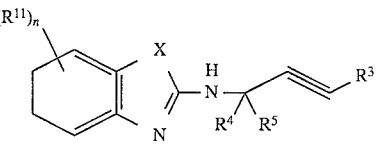

wherein $R^3$, $R^4$, and $R^5$ are independently hydrogen or an unsubstituted alkyl group having less than 12 carbon atoms or an unsubstituted phenyl group; and X is oxygen, sulfur, or selenium;

$R^{11}$ is independently hydrogen or halogen atoms, or alkyl, alkoxy, carboxy, phenyl or cyano groups, and n is 0, 1 or 2;

comprising combining a compound of the following structure (A):

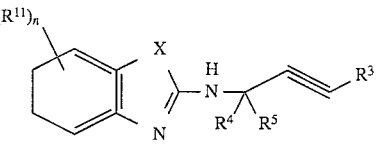

wherein X, $R^3$, $R^4$, $R^5$, $R^{11}$, and n are as previously defined, with a catalytic amount of silver or gold cation catalyst at a temperature of less than about 50° C. and in the presence of an organic solvent, to form compound (I).

2. A process according to claim 1 wherein $R^{11}$ is independently an alkyl group.

3. A process according to claim 1 wherein $R^4$ and $R^5$ are hydrogen.

4. A process according to claim 1 wherein the cation catalyst is silver.

5. A process according to claim 1 wherein the cation catalyst is gold.

6. A process according to claim 1 wherein the formation of the dihydropyrimidine compound occurs at a temperature of between about 10° and about 25° C.

7. A process according to claim 6 wherein the formation of the dihydropyrimidine compound occurs at a temperature of between about 12° and 20° C.

8. A process of synthesizing a dihydropyrimidine compound, said process comprising reacting an alkynylamine or its ammonium salt, said alkynylamine having the structure:

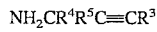

wherein $R^3$, $R^4$ and $R^5$ are independently hydrogen or an unsubstituted alkyl group having less than 12 carbon atoms or an unsubstituted aryl group; with a compound having the structure (III):

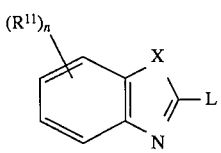

wherein $R^{11}$ is independently hydrogen or halogen atoms, or alkyl, alkoxy, carboxy, phenyl or cyano groups and n is 0, 1 or 2;

X is oxygen, sulfur, or selenium; and

L is a leaving group; to form a heterocyclic alkynylamine having the structure (A):

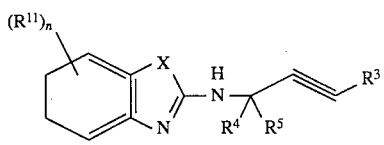

wherein X, $R^3$, $R^4$, $R^5$, and $R^{11}$, and n are as previously defined; and reacting the heterocyclic alkynylamine at a temperature of less than about 50° C. with a silver or gold cation catalyst in an organic solvent to form a dihydropyrimidine compound having the structure (I):

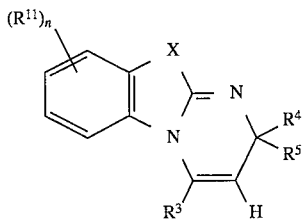

wherein X, $R^3$, $R^4$, $R^5$, $R^{11}$, and n are as previously defined.

9. A process according to claim 8 wherein $R^{11}$ is independently an alkyl group.

10. A process according to claim 8 wherein $R^4$ and $R^5$ are hydrogen.

11. A process according to claim 8 wherein the formation of the dihydropyrimidine compound occurs at a temperature of between about 10° and about 25° C.

12. A process according to claim 11 wherein the formation of the dihydropyrimidine compound occurs at a temperature of between about 12° and 20° C.

* * * * *